(12) United States Patent
Willson, III et al.

(10) Patent No.: US 6,617,108 B1
(45) Date of Patent: Sep. 9, 2003

(54) METHODS AND COMPOSITIONS FOR BIOTECHNICAL SEPARATIONS USING SELECTIVE PRECIPITATION BY COMPACTION AGENTS

(75) Inventors: Richard C. Willson, III, Houston, TX (US); Jason Murphy, Houston, TX (US)

(73) Assignee: Technology Licensing Co. LLC, Palm Harbor, FL (US)

( * ) Notice: Subject to any disclaimer, the term of this patent is extended or adjusted under 35 U.S.C. 154(b) by 0 days.

(21) Appl. No.: 09/609,996

(22) Filed: Jul. 3, 2000

Related U.S. Application Data

(60) Provisional application No. 60/143,768, filed on Jul. 12, 1999.

(51) Int. Cl.[7] .......................... C12Q 1/68; C12P 19/34; C07H 21/02
(52) U.S. Cl. ........................ 435/6; 435/91.2; 536/23.1; 536/24.5; 536/24.3
(58) Field of Search ................... 435/6, 91.2; 536/23.1, 536/24.3, 24.5

(56) References Cited

U.S. PATENT DOCUMENTS

| | | |
|---|---|---|
| 5,576,196 A | 11/1996 | Horn et al. |
| 5,622,822 A | 4/1997 | Ekeze et al. |
| 5,707,812 A | 1/1998 | Horn et al. |

OTHER PUBLICATIONS

Kieser, "Factors affecting the isolation of CCC DNA from streptomyces lividans and *Escherichi coli*", Plasmid 12:19–36, 1984.*
Raspaud et al, "Precipitation of DNA by polyamines: A polyelectrolyte behavior", Biophys. J. (1998) 74:381–393.*
Parasrampuria Thera, issues in Gene Therapy Biopharm II: 38–45 (1998).
Anderson Human Gene Therapy, Nature 392 (1998) 25–30.
Horn Human Cancer Gene Therapy: Gene Ther.6 (1995) 565–573.
Gosule Compact form of DNA Nature 259 (1976) 333–335.
Arscott Condensation of DNA Biopolymers 30 (1990) 619–630.
Wilson Counter Ion Induced (1979) Biochem 18, 2196.
Furret J. Mole. Biol. 234 (1994) 825–847.
Rolland Crit Review of (1998) Drug 15 pp 143–198.
Hoopes Nucleaic Acids Res. (1981) 9 pp 5493–5504.
Sambook Mole, Cloning a Lab. Manual (1989) 2nd. ed.
Lez Anal. Biochem 160 (1987) pp 332–336.
Horn et al US Pat. 5 707, 812 (See "US Pat Doc's").
Hubert et al J. Chromato. 184 (1980) pp 325–333.
Irwin et al Essays in Biochem (1995) 29 pp 137–156.
Widom et al Biopolymers ZZ (1983) 1595–1620.
Nunn et al J. Mol. Biol. 256 (1996) 340–351.
Kieft et al Structure 5 (5) (1997) 713–721.
Pitulle et al Appl. & Envir Micro (1995) biology 61 (10) 3661–3666.
Setterquist Gene183(1–8) (1996) 237–242.
Yang et al Gene 95 (1996) 81–85.
Sioud et al Proc. Natl Acad Sci. 88 (1991) 7303–7307.
Couture Trends in Genetics 12 (1996) (12) 510–514.
Christoffsen J. of Med. Chem 38 (1995) (12) 2023–2037.
Weiss Cell. Mol. Life Sci (1999) 55 334–358.
Kumar Microbiol. and Mole, (1998) Biol, Rev. 62(41)415–1434.
Matthews Bioessays 15 (8) (1993) 561–566.
Hedemstierna System.Appl.Micro (1993) biol. 16 280–286.
Pitulle Sys. Appl. Microbiol. (1997) 20 133–136.
Uchiyama et al Biochem 90 (1981) 643–648.
Lee et al Preparative Biochem, (1986) 16(3) 247–258.
Hori J. Chromatography (1990) 515 611–619.
Fair et al AppliedEnvirMicrob.21 (1971) 16–8.
Scopes Springer–Verlag (1993) 379 pp.
Blackburn et al Nucleic Acids in Chem. (1996) and Biol. pp 337–346.
Saenger Prin of NucleicAcid (1988) structure pp432–434.
Ma et al Biochem. 34(11) (1995) 3521–3528.

* cited by examiner

*Primary Examiner*—Jeffrey Fredman
(74) *Attorney, Agent, or Firm*—Richard Coale Willson, Jr.

(57) ABSTRACT

Preferred embodiments of the invention include purification of DNA, preferably plasmid DNA, by use of selective precipitation, preferably by addition of compaction agents. Also, included is a sealable method for the liquid phase separation of DNA from RNA. RNA may also be recovered by fractional precipitation according to the invention. Applicants have discovered that RNA, commonly the major contaminant in DNA preparations, can be left in solution while valuable purified plasmid DNA is directly precipitated. Additional aspects of the invention include minipreps, preferably of plasmid and chromosomal DNA, to obtain sequenceable and restriction digestible DNA in high yields in multiple simultaneous procedures. Still further aspects disclose enhanced stripping of the compaction agent by a stripping method comprising high salt addition and pH shift, and combinations of these techniques. Also, disclosed is a method of assay in which a labeled probe is precipitated when it is hybridized to a target, (e.g. chromosomal DNA, oligonuclotides, Ribosomal RNA, tRNA), and thereafter precipitating the probe/target complex with compaction agents and leaving in solution any unhybridized probe. For example, chromosomal DNA, plasmid, ribosomal RNA, and oligonucleotides can be recovered in excellent purity; by then heating the mixture of nucleic acids (above their melting temperature if the hybridization site is buried within secondary structure) and thereafter precipitating the probe and the target.

33 Claims, 9 Drawing Sheets

FIGURE 1. STRUCTURES OF COMMON COMPACTION AGENTS

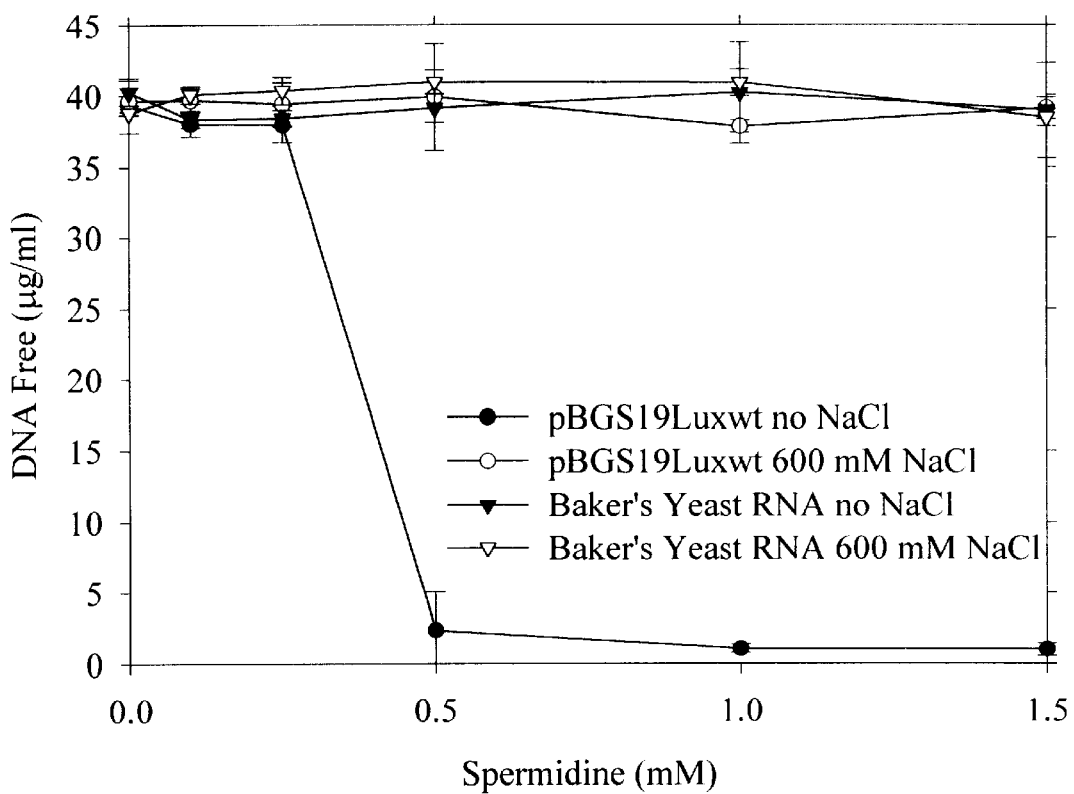
Figure 2. Precipitation by spermidine of 40 μg/mL pBGS19Luxwt or Baker's yeast RNA in 10 mM Tris buffer at pH 8.0 with and without 600 mM NaCl. Error bars are +/- one standard deviation.

Fig. 3

Lane #

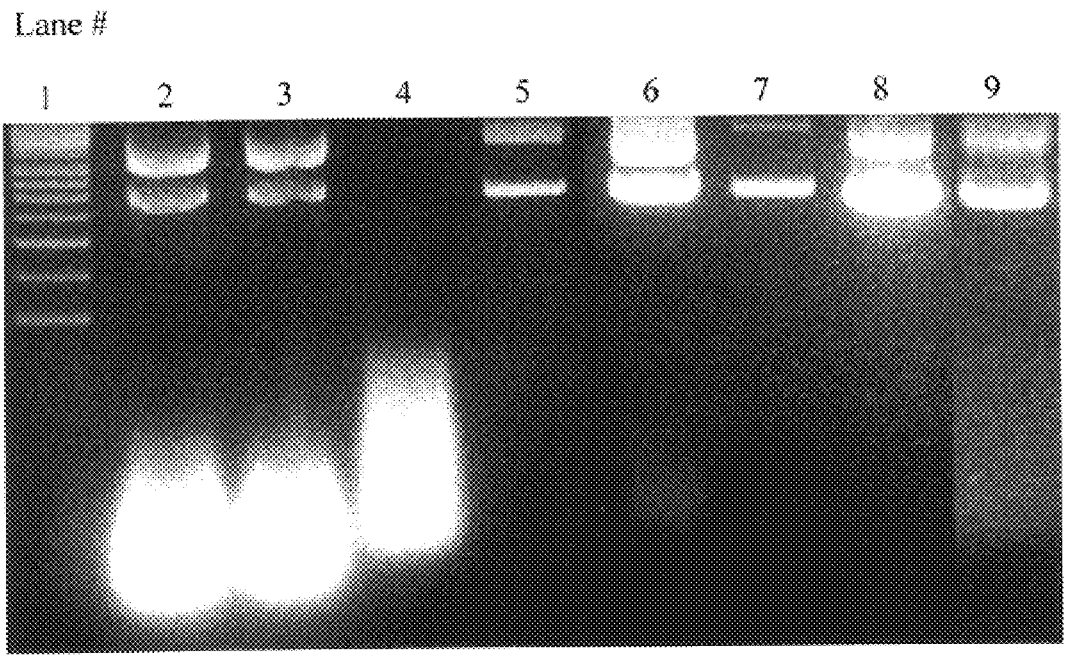

Figure 3. 1% agarose gel that traces the large-scale purification of pBGS19luxwt. Lane 1 is a supercoiled plasmid ladder from Gibco; Lane 2 is the preparation after Celite filtration, isopropanol precipitation, and resuspension; Lane 3 is the supernatant after LiCl precipitation; Lane 4 is the supernatant of the compaction precipitation; Lane 5 is the resuspended pellet of the compaction precipitation; Lane 6 is a 10X loading of the material in Lane 5; Lane 7 is after a Q sepharose anion exchange column (Fig. 5, bottom, Peak 5); Lane 8 is a 10X loading of Lane 7 and Lane 9 is pBGS19Luxwt plasmid DNA separated using the mini-prep procedure.

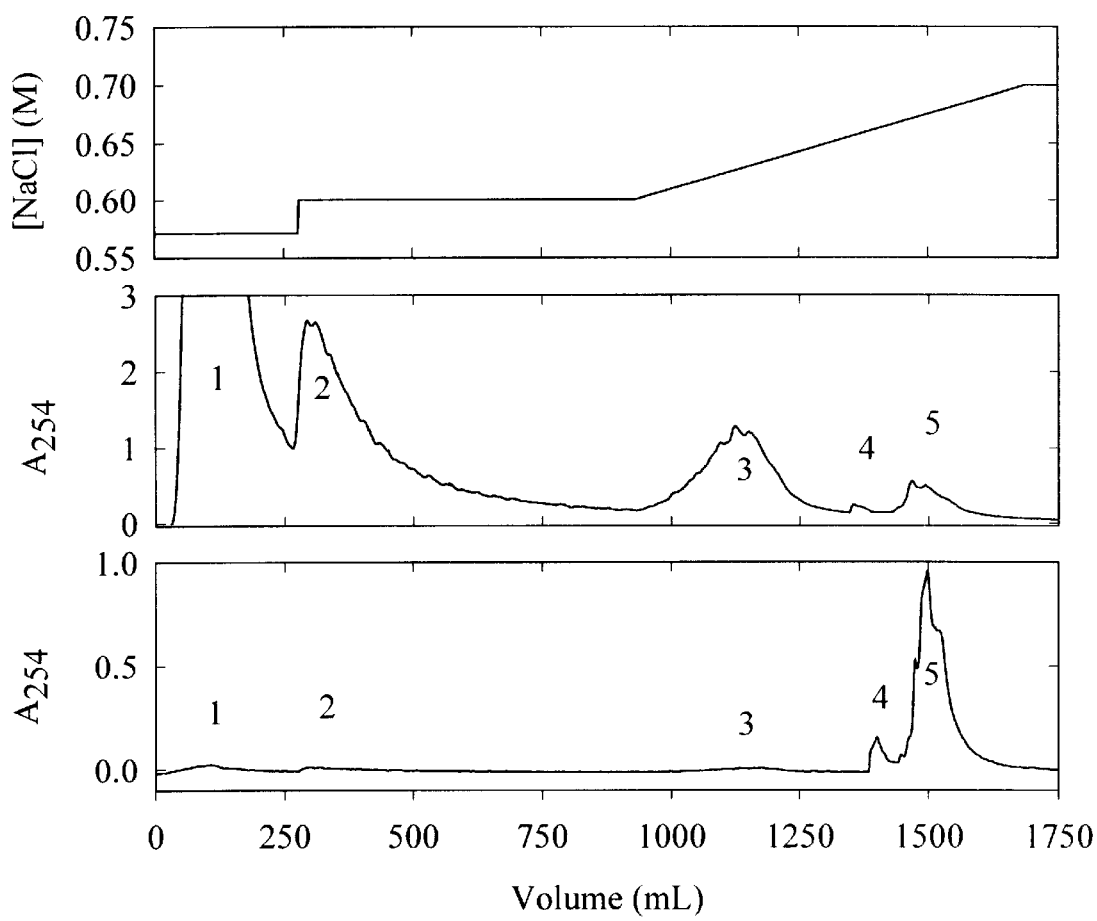
Figure 4. FPLC anion-exchange separation of pBGS19Luxwt of an alkaline lysate after isopropanol and LiCl precipitation. Top: NaCl gradient; Middle: with no previous compaction precipitation step; Bottom: identical separation after a previous compaction precipitation step.

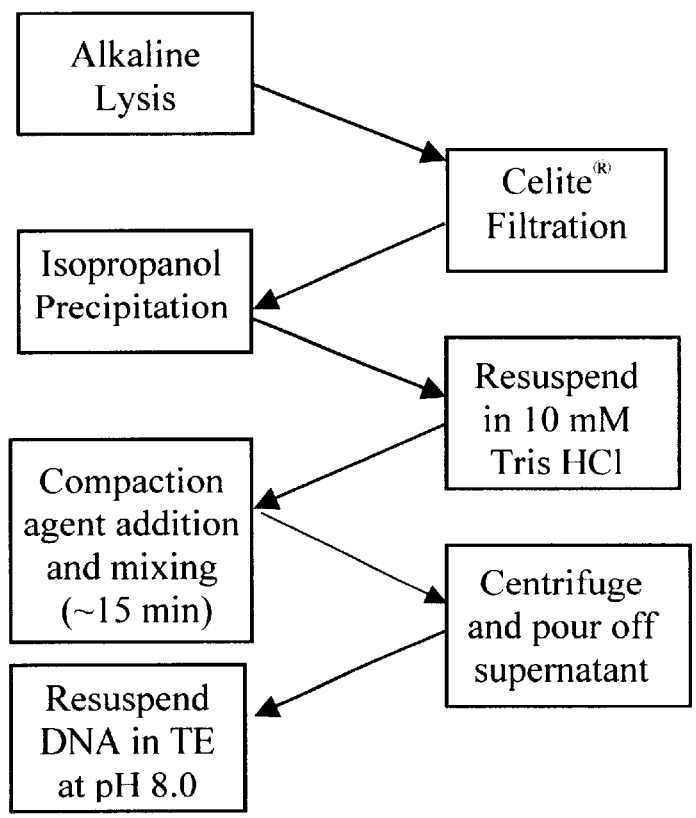
Figure 5. Summary of a selective precipitation-based noncolumn DNA purification as detailed in example 1.

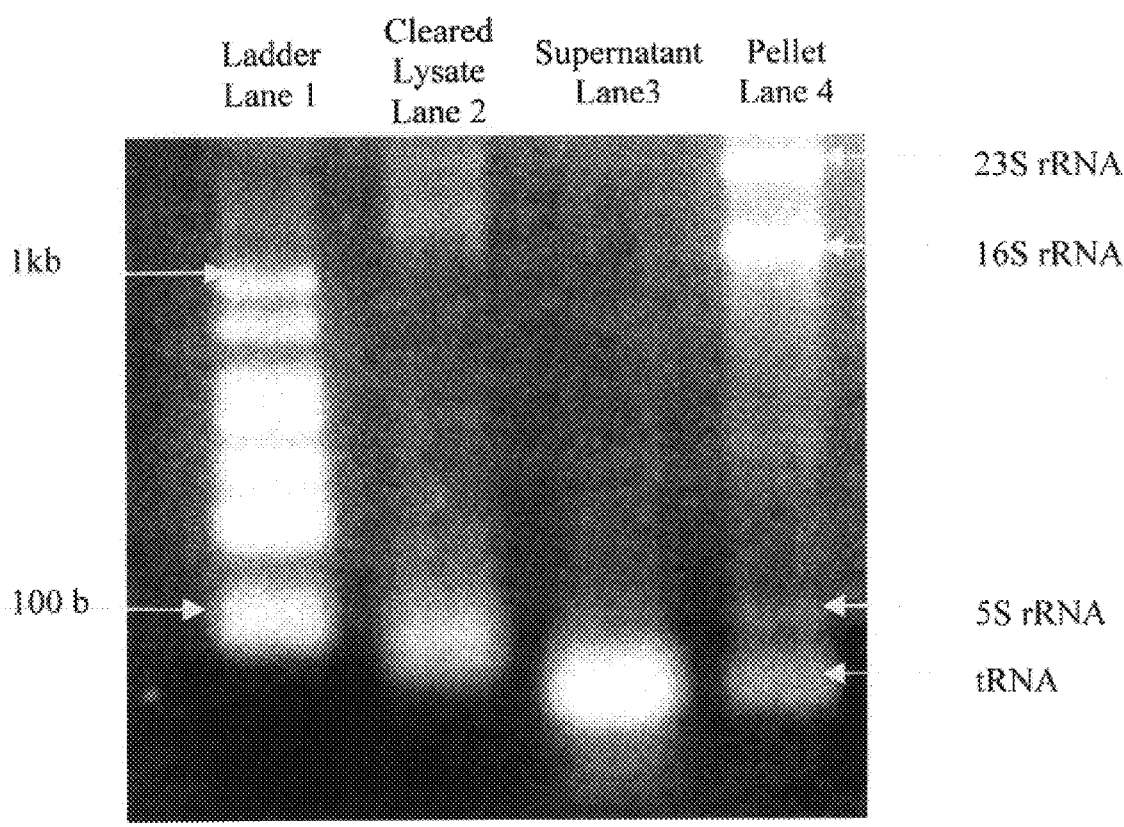

Figure 6. 3% biogel (from Bio101 Inc.) of *V. proteolyticus* RNA purified by Example 9. Lane 1 is the Ambion RNA Century Plus Size Markers; Lane 2 is the lysate after BPER addition, spermidine addition and centrifugation; Lane 3 is the supernatant of the 4 mM hexammine cobalt precipitation; and Lane 4 is the RNA pelleted in the hexammine cobalt precipitation but before any column separation.

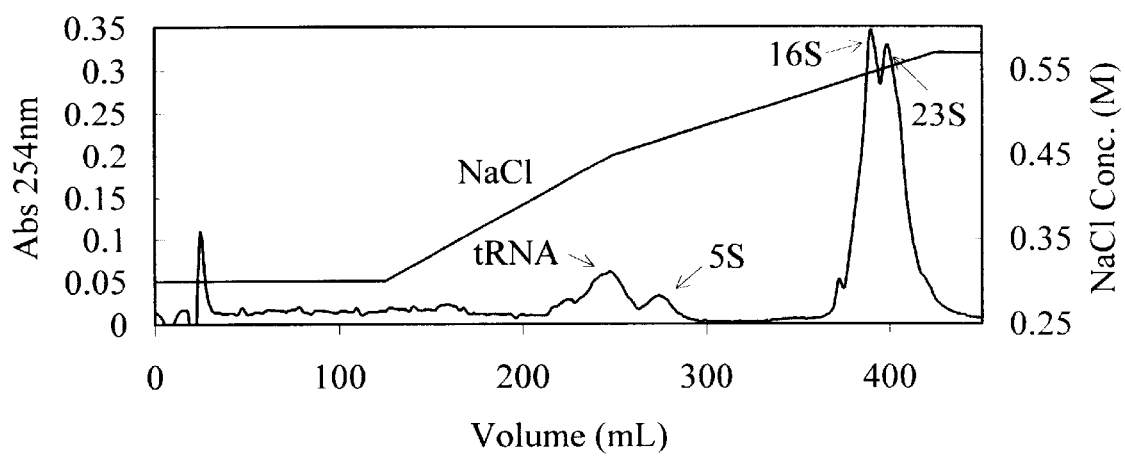
Figure 7. FPLC chromatogram of *V. proteolyticus* RNA on and 25 mL high performance Q Sepharose anion-exchange column (Pharmacia). The gradient was run over 12 column volumes from 0.30 M NaCl to 0.57 M NaCl in a column buffer of 20 mM bis-tris propane and 20 mM EDTA at pH 6.9.

Figure 8. FPLC chromatogram of pCP3X3 aRNA containing *E. coli* strain JM109 on and 25 mL high performance Q Sepharose anion-exchange column (Pharmacia). The gradient was run over 12 column volumes from 0.37 M NaCl to 0.57 M NaCl in a column buffer of 20 mM bis-tris propane and 20 mM EDTA at pH 6.9.

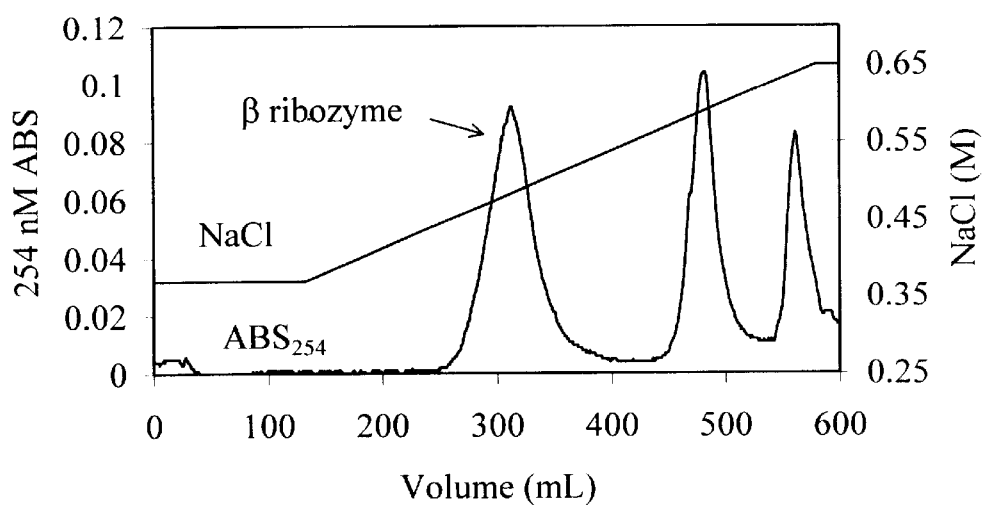
Figure 9. FPLC chromatogram of selective precipitation purified β ribozyme on and 25 ml high performance Q Sepharose anion-exchange column (Pharmacia). The gradient was run over 12 column volumes from 0.37 M NaCl to 0.7 M NaCl in a column buffer of 10 mM bis-tris propane and 2 mM EDTA at pH 6.9.

METHODS AND COMPOSITIONS FOR BIOTECHNICAL SEPARATIONS USING SELECTIVE PRECIPITATION BY COMPACTION AGENTS

Continuation of prior application No. 60/143,768 filed on Jul. 12, 1999.

BACKGROUND OF THE INVENTION

I. Field of the Invention

The present invention relates to the general field of biochemical assays and separations, generally classified in U.S. Patent Class 435.

II. Description of the Prior Art

Interest in nucleic acid purification has increased with human trials of plasmid-based vaccines (e.g., for influenza, HIV, and malaria) and therapeutics (e.g., insulin and vascularization promoters) as well as the steady expansion of DNA sequencing activities. (references 1 and 2) This invention embodies a rapid, scaleable, nuclease-free (preferably RNAse free), cost effective method of nucleic acid purification using selective precipitation by compaction agents.

Prior Art will include the following:

1. Parasrampuria, D. and Hunt, A., (1998), Therapeutic issues in gene therapy; part 1: vectors. Biopharm. 11:38–45.
2. Anderson, F., (1998), Human Gene Therapy. Nature. 392: 25–30.
3. Horn, N. A., Meek, J. A., Budahazi, G., and Marquet M. 1995. Cancer gene therapy using plasmid DNA: purification of DNA for human clinical trials. Human Gene Therapy. 6:565–573.
4. Gosule, L. C. and Schellman, J. A., (1976), Compact form of DNA induced by spermidine. Nature. 259:333–335.
5. Arscott, P. G., Li, A. Z., and Bloomfield, V. A., (1990), Condensation of DNA by trivalent cations. 1. Effects of DNA length and topology on the size and shape of condensed particles. Biopolymers. 30:619–630.
6. Wilson, R. W. and Bloomfield, V. A., (1979), Counter-ion induced condensation of deoxyribonucleic acid. A light scattering study. Biochemistry. 18:2192–2196.
7. Bednar, J., Furrer, P., Stasiak, A., Dubochet, J., Egelman, E. H., and Bates, A. D., (1994), The twist, writhe and overall shape of supercoiled DNA change during counterion-induced transition from a loosely to a tightly interwound superhelix: possible implications for DNA structure in vivo. Journal of Molecular Biology. 235:825–847.
8. Rolland, A., (1998), From genes to gene medicines: recent advances in nonviral gene delivery. Critical Review of Therapeutic Drug Carrier Systems. 15:143–198.
9. Hoopes, B. C. and McClure, W. R., (1981), Studies on the selectivity of DNA precipitation by spermine. Nucleic Acids Research. 9:5493–5504.
10. Sambrook, J., Fritsch, E. F., and Maniatis, T., (1989), Molecular cloning, a laboratory manual. Second edition, Cold Spring Harbor Laboratory Press.
11. Horn, N., Marquet, M., Meek, J., and Budahazi, G., (1996), Process for reducing RNA concentration in a mixture of biological material using diatomaceous earth. U.S. Pat. No. 5,576,196.
12. Lev, Z., (1987), A procedure for large-scale isolation of RNA-free plasmid and phage DNA without the use of RNAse. Analytical Biochemistry. 160:332–336.
13. Drevin, I., Larsson, L., and Johansson, B. L., (1989), Column performance of Q-Sepharose HP in analytical- and preparative-scale chromatography. Journal of Chromatography. 477:337–344.
14. Horn et al; U.S. Pat. No. 5,707,812, Purification of Plasmid DNA During Column Chromatography, which is understood to teach addition of short chain polymeric alcohol to promote isolation of plasmid DNA.
15. Hubert, P., and Dellacherie, E., (1980), Use of water-soluble biospecific polymers for the purification of proteins, Journal of Chromatography, 184, 325–333.
16. Irwin, J. A., and Tipton, K. F., (1995), Affinity precipitation: a novel approach to protein purification, Essays in Biochemistry, 29, 137–156.
17. Widom, J., and Baldwin, R. L., (1983), Monomolecular condensation of λ-DNA induced by Cobalt Hexammine, Biopolymers, 22, 1595–1620.
18. Nunn, C. S., and Neidle, S. 1996. The high resolution crystal structure of the DNA decamer d(AGGCATGCCT). J. Mol. Biol. 256:340–351.
19. Kieft, J. S. and Tinoco, I. 1997. Solution structure of a metal-binding site in the major groove of RNA complexed with cobalt (III) hexammine. *Structure.* 5(5):713–721.
20. Pitulle, C., Hedenstierna, K. O., and Fox, G. E. 1995. A novel approach for monitoring genetically engineered microorganisms by using artificial, stable RNAs. Applied Environmental Microbiology. 61(10): 3661–3666.
21. Setterquist, R. A, Smith, G. K., Oakley, T. H., Lee, Y. H., and Fox, G. E. 1996. Sequence, overproduction and purification of Vibrio proteolyticus ribosomal protein L18 for in vitro and in vivo studies. Gene. 183(1-2):237–242.
22. Yang, Y. and Fox, G. E. 1996. An Archaea 5S rRNA analog is stably expressed in *Escherichia coli*. Gene. 168: 81–85.
23. Sioud, M. and Drlica, K. 1991. Prevention of human immunodeficiency virus type 1 integrase expression in *Escherichia coli* by a ribozyme. Proc. Natl. Acad. Sci. USA 88:7303–7307.
24. Couture, L. A. and Stinchcomb, D. T. 1996. Anti-gene therapy: the use of ribozymes to inhibit gene function. TIG. 12(12):510–514.
25. Christoffersen, R. E., and Marr J. J., (1995), Ribozymes as human therapeutic agents, Journal of Medicinal Chemistry, 38(12), 2023–2037.
26. Weiss, B., Davidkova, G. and Zhou L. W., (1999), Antisense RNA gene therapy for studying and modulating biological processes, Cell. Mol. Life Sci., 55, 334–358.
27. Kumar, M. and Carmichael, G. G., (1998), Antisense RNA: function and fate of duplex RNA in cells of higher eukaryotes, Microbiology and Molecular Biology Reviews, 62(4), 1415–1434.
28. Matthews, H. R., (1993), Polyamines, chromatin structure and transcription, BioEssays, 15(8), 561–566.
29. Hedemstierna, K. O. F., Lee, H. Y., Yang, Y., and Fox, G. E, (1993), A prototype stable RNA identification cassette for monitoring plasmids of genetically engineered microorganisms. System. Appl. Microbiol. 16, 280–286.
30. Pitulle, C., Dsouza, L., and Fox, G. E. 1997. A low molecular weight artificial RNA of unique size with multiple probe target regions. System. Appl. Microbiol. 20:133–136.
31. Uchiyama, S., Imamura, T., Nagai, S., and Konishi, K. 1981. Separation of low molecular weight RNA species by high-speed gel filtration. J. Biochem. 90:643–648.
32. Lee, K. M. and Marshall, A. G. 1986. High-speed preparative-scale separation and purification of ribosomal 5S and 5.8S RNA's via Sephacryl S-300 gel filtration chromatography. Preparative Biochemistry 16(3) :247–258.

33. Hori, S. and Ohtani, S. 1990. Separation of high-molecular mass RNAs by high-performance liquid chromatography on hydroxyapatite. Journal of Chromatography. 515:611–619.
34. Fair, W. R., and Wehner, N., (1971) Antibacterial action of spermine: effect on urinary tract pathogens, Applied Environmental Microbiology, 21(1), 6–8
35. Scopes, R. K., (1993) Protein purification: principles and practice, Springer-Verlag, 379 pages.
36. Blackburn, G. M., and Gait, M. J., (1996), *Nucleic Acids in Chemistry and Biology*, Oxford University Press, pages 337–346.
37. Saenger, W., (1988), *Principles of Nucleic Acid Structure*, Springer-Verlag, pages 432–434.
38. Ma, C., Sun, L., and Bloomfield, V. A., (1995), "Condensation of Plasmids Enhanced by Z-DNA Conformation of d(CG)$_n$ Inserts", Biochemistry, vol. 34(11), 3521–3528.
39 U.S. Pat. No. 5,622,822, to Tobias et al, Issued Apr. 22, 1997, (Assigned Johnson & Johnson), Methods for capture and selective release of nucleic acids using polyethyleneimine and an anionic phosphate ester surfactant and amplification of same teaches that nucleic acids can be made available for amplification or other treatment after lysis by contacting the lysate with polyethyleneimine to form a precipitate with the nucleic acids. The nucleic acids are then released from the precipitate by contact with a strong base, and the released nucleic acids are kept in solution with an anionic phosphate ester surfactant.

II. Problems Presented by Prior Art

Most current methods of plasmid separation are relatively time-consuming and require the use of adsorbents, toxic substances, nucleases, and/or filtration media to separate plasmid from protein, genomic DNA, endotoxins and especially the abundant RNA present in cell lysates.

This technique offers several important improvements over current methods: no RNAse and/or other enzymes are used, the technique requires no chromatographic medium, and the technique is directly scaleable if larger quantities of plasmid DNA are needed.

Also with the use of different compaction agents, different types of nucleic acids can be separated from the same mixture. The invention can separate different types of RNA and DNA as long as some secondary structure is present.

In addition RNA can be fractionated based on molecular weight via selective precipitation.

Different compaction agents also have different affinities for different nucleic acids. For example hexammine cobalt has a higher affinity for RNA than the polyamine spermidine so multiple step selective precipitations have been developed to help separate nucleic acids as quickly as possible.

The method can also be used for parallel purification of a large number of samples (mini-preps) and is readily adaptable to automation (robotics).

In another embodiment, the invention also provides a method for making a biochemical assay by hybridizing a labeled probe to a target (e.g. chromosomal DNA, oligonucleotides, Ribosomal RNA, tRNA, plasmid, aptamer, viral RNA), and thereafter precipitating the probe/target complex with compaction agents. For example, preparing a mixture containing chromosomal DNA, plasmid, ribosomal RNA, and labeled oligonucleotides, then heating the mixture of nucleic acids above their melting temperature (if the hybridization site is buried within secondary structure) and thereafter precipitating the probe and the target).

In another embodiment, the invention also provides a method for separating a nucleic acid-binding protein from a mite containing the protein and its nucleic acid binding partner and other components, by precipitating the bound nucleic acid, carrying the associated protein into the precipitate, from which it may optionally be further purified. For example, a selected protein might be isolated from cultured human cells containing both the protein and a DNA sequence to which the protein binds, by making a lysate from the cells and precipitating the DNA, producing a precipitate enriched in both the DNA target sequence and in the binding protein.

Bioseparations, especially separation of RNA from DNA or vice versa, are conventionally accomplished in bench scale or larger pilot plants in which a fermentation is carried out to produce cell mass which is lysed, then exposed to filtration and the use of nucleases to reduce unwanted nucleic acid populations (e.g. the use of ribonuclease (RNAse) in plasmid purification). Generally, after these initial solution phase purification steps, the effluent products are further purified by chromatographic columns (e.g. anion-exchange or size-exclusion chromatography), often with samples being analyzed and results subjected to quality control feedback techniques. Such procedures can take a day or more for a single run or batch on a single mixture, assuming the optimum conditions, concentrations, etc. The present invention permits the separation of dozens of feed mixtures in a single set-up, often in less time than required for a single separation by conventional methods. Further, when practiced in its preferred embodiments, the invention can sharply reduce the production costs (costs per milligram of purified DNA product produced).

In addition, the labeled probe precipitation embodiment offers a new method for hybridization assays without the use of radiolabeled probes or the use of solid supports. Using compaction precipitation, when a tagged probe (e.g. fluoresceinated, radioactively tagged, etc.) is added to a solution containing its target a double stranded nucleic acid is formed and this new structured hybrid can be selectively precipitated while the single stranded probe will be left in solution.

In addition, the nucleic acid/binding protein coprecipitation embodiment offers a new method of identifying and/or separating nucleic acid-binding proteins from cells expressing them. Using compaction precipitation, these proteins can be selectively precipitated away from other proteins, producing a significant degree of selective enrichment without the need to prepare costly affinity adsorbent matrices.

Summarizing, preferred embodiments include the assay, the protein purification, and selectivity for DNA precipitation over RNA, and isolation of RNA by first precipitating DNA, then separately precipitating RNA in a second step.

SUMMARY OF THE INVENTION

General Statement of the Invention

According to the invention, in preferred embodiments, DNA, preferably plasmid DNA, is readily purified, by use of selective precipitation, preferably by addition of compaction agents. Also included is a scaleable method for the liquid-phase separation of DNA from RNA. RNA may also be recovered by fractional precipitation according to the invention.

We have discovered that RNA, commonly the major contaminant in DNA preparations, can be left in solution while valuable purified plasmid DNA is directly precipitated.

Additional aspects of the invention include mini-preps, preferably of plasmid and chromosomal DNA to obtain sequenceable and restriction digestible DNA in high yields in multiple simultaneous procedures.

Still further aspects disclose enhanced stripping of the compaction agent by a stripping method comprising high salt addition and pH shift, and combinations of these techniques.

Also disclosed is a method of assay in which a labeled probe is precipitated when it is hybridized to a target, (e.g. chromosomal DNA, oligonucleotides, Ribosomal RNA, tRNA), and thereafter precipitating the probe/target complex with compaction agents and leaving in solution any unhybridized probe. For example, chromosomal DNA, plasmid, ribosomal RNA, and oligonucleotides can be recovered in excellent purity; by then heating the mixture of nucleic acids and probe (above their melting temperature if the hybridization site is buried within secondary structure) and thereafter precipitating the probe and the target, whereby the target can be detected.

Further disclosed is a method for producing a reduced-viscosity cell lysate, useful as a starting point for further purification of product by removal of nucleic acids through compaction precipitation.

Each of these parameters is discussed below:

A new method for DNA separation has been developed using selective precipitation with small-molecule compaction agents, such as spermine and spermidine, which bind in the grooves of a double-stranded DNA molecule. Compaction precipitation uses compaction agents to neutralize the highly charged phosphate backbone of nucleic acids and to stabilize intermolecular interactions leading to precipitation. This selective precipitation has been demonstrated to separate double-stranded plasmid DNA from RNA, protein and other contaminants in solution. Using compaction precipitation, we have also developed an improved mini-prep procedure capable of producing sequencing-grade plasmid DNA. The precipitation of nucleic acids from lysates can also be applied to the clarification of protein lysates before any subsequent chromatography is done.

In addition a compaction agent-based selective precipitation of RNA from clarified lysates of bacteria, fungi, or metazoan cells and/or mixtures of biomolecules has been developed. The use of selective precipitation with compaction agents and anion-exchange chromatography have been shown to effectively separate the ribosomal RNA's from each other and 5S rRNA from tRNA. Compaction agent-based separation of RNA produces either a total RNA mixture or a high molecular weight RNA fraction with little contaminating protein or DNA. Anion-exchange chromatography is then used to separate the different RNA molecules from the total bacterial RNA sample. Also, using compaction precipitation and labeled oligonucleotide probes, a hybridization assay has been developed for use in a wide variety of applications, including e.g. environmental monitoring, quality control of nucleic acids, medical diagnostics, and use in mutation studies.

Still another embodiment comprises a method of isolating nucleic acid-binding proteins by coprecipitating them with the nucleic acids to which they bind has been developed. This method can be used in purification and identification of regulatory proteins, histones, and aptamers, for example.

Cell Mass

The starting material is often a mass of cells prepared by fermentation or cell culture, isolated from the environment, or derived from tissues. The cells are then disrupted so the nucleic acids go into solution, forming a lysate. The lysate then optionally undergoes an alkaline lysis or other process to form a clarified lysate. The preferred feed to the compaction precipitation step is a clarified lysate or synthetic mixture. A variety of cell types can be used as feed for this whole process, with bacterial, yeast, other eukaryotic, Gram-negative and Gram-positive being preferred and Gram-negative being most preferred.

Product

The product of the invention can be purified DNA, RNA or nucleic acid-binding proteins, preferably DNA, and most preferably plasmid DNA, e.g. as used in preparation of influenza or other vaccines. Alternative preferred product is RNA, preferably ribosomal RNA, ribozymes, aptamer, artificial RNA, and any other RNA based molecule.

Particularly preferred is RNAse-free plasmid having a quantity of nucleases below current limits of detection and/or low endotoxin contamination. In other embodiments, the product can be a bioassay or protein, e.g. as produced in Examples 13 and 16.

In general, the selective precipitation of the invention can be applied to all bacteria (Gram-negative, Gram-positive and Archaea), all eukaryotes (such as yeast and human cells), recombinant cells, and all synthetic nucleic acids. The invention can separate YAC's (yeast artificial chromosomes). YACs are very large plasmids in yeast, used in sequencing projects. The invention can also be applied to the production of cosmids (basically very large plasmids in general), and phage and other viral DNA, and the detection of protein-nucleic acid binding and viruses.

Compaction Agents

The compaction agents are preferably small, cationic molecules, which bind in either the major or minor grooves of a double-stranded RNA or DNA molecule, reducing the volume occupied by the nucleic acid. FIG. 1 shows the structures of some common compaction agents). Some compaction agents function in vivo to package genomic DNA into sperm (see reference 7), and can also serve a similar function in the delivery of DNA pharmaceuticals. (See reference 8).

Compaction of DNA involves charge neutralization in combination with stabilization of inter-helix interactions. The compaction agent binds in either the major or minor groove, in proximity to the negatively charged phosphate groups. Precipitation occurs when adjacent DNA helices are affected simultaneously, with the compaction agent not only reducing the helix-helix repulsion but also bridging the helixes. Hoopes described this phenomenon in 1981 (see reference 9) but upon further investigation, we have discovered that RNA is far less readily precipitated by certain compaction agents, preferably linear polyamine type compaction agents, and found that RNA can be selectively precipitated and even fractionated using specialized compaction agents, most preferably, hexammine cobalt as the compaction agent and/or without substantial precipitation of contaminating endotoxins.

In general, there will be added about 0.1 to 20, more preferably about 0.2 to 15 and most preferably about 0.3 to 5 mM of a compaction agent, preferably selected from the group consisting of: basic polypeptides (e.g. polylysine), polyamines (e.g. protamine, spermidine, spermine, putrescine, cadaverine, etc.), trivalent and tetravalent metal ions (e.g. hexammine cobalt, chloropentammine cobalt, chromium (III)), netropsin, distamycin, lexitropans, DAPI (4',6 diamino 2-phenylindol), berenil, pentamidine, manganese chloride. At present knowledge, the moieties in parenthesis will be more preferred, but any other molecule that can be used to compact DNA via the mechanism described above may be used according to the product to be produced and the cell mass available.

Many other agents may be considered compaction agents and these include: basic polypeptides (i.e. polylysine), polyamines (i.e. protamine, spermidine, spermine, cadaverine, etc.), trivalent and tetravalent metal ions (i.e. hexammine cobalt, chloropentaminie cobalt, chromium (III)), netropsin, distamycin, lexitropans, DAPI (4', 6 diamino 2-phenylindol), berenil, pentamidine, manganese chloride, or any other molecule that can be used to compact DNA via the mechanism described above (see references 1–7, 9,17–19, 36,37,38). Also any protein having multiple binding domains for nucleic acids can potentially, for large complexes, result in the precipitation of nucleic acids.

Lysing Agents

Lysing agents, preferably detergents, more preferably nonionic detergents, are used to break down cell membranes, thus releasing DNA, RNA and proteins from the cells. The most preferred lysing agent for plasmid DNA is the alkaline lysis detailed in Example 1. The most preferred lysing agent for RNA is Bacterial Protein Extraction Reagent (BPER) which has an unknown composition (it is a proprietary mixture of nonionic detergents marketed by the Pierce Chemical Company), but other nonionic detergents are useful and many detergents are operable, even some anionic and cationic detergents under certain applications. The nonionic detergent lysing agents will generally be added to the cell mass in a concentration of about 0.1 to 5, more preferably 0.5 to 2 wt %. Other known lysing agents can also be used with the technology such as freeze/thawing, French cell press, enzymes, microfluidization, sonication, etc.

Nucleases

One of the main advantages of the compaction precipitation technology is that it circumvents the need to use nucleases, proteases or carbohydrases. Selective precipitation directly harvests nucleic acids and the target nucleic acid of a precipitation can be changed by changing conditions (i.e. type of compaction agent, quantity of compaction agent, concentration of salts, etc.) Because of this selectivity other large biomolecular contaminants such as proteins, unwanted nucleic acids, carbohydrates, etc. do not have to be degraded by enzymes. Thus the use of RNAse, DNAse, proteases, and other enzymes is unnecessary.

pH

All Examples are carried out at a pH between 6–8, to keep nucleic acid degradation to a minimum, though other pHs may be preferred in certain cases. The compaction agents can be affected by extreme pH. In fact, we have found that pH change (e.g., shifting the pH past the $pK_A$ of the amine groups in polyamines, so that they lose their positive charge and do not bind nucleic acids strongly is one of the ways to separate nucleic acids from the compaction agents themselves.)

Ionic Strength

High ionic strength can negate the effects of compaction agents. The preferred maximum ionic strength for compaction precipitation is 250 mM NaCl when plasmid is precipitated in 10 mM spermine. More preferred ionic strength before compaction agent addition is about 0–50 mM, more preferably 1 to 20 mM but those skilled in the art will adjust the ionic strength to best suit the particular lysate and compaction agents being employed. Changing ionic strength is an easy way to separate the compaction agents from the nucleic acids, because in the presence of a high ionic strength solution the compaction agents are displaced from the nucleic acid backbone.

Hybridizing

To hybridize means to bind to its complementary sequence in the target. If the probe used in a bioassay includes a sequence 5'-AAGC-3'; its hybridizing complementary sequence will be 5'-GCTT-3'. This is important because this test can be run as a valuable quality control measure on oligonucleotides and other synthetic nucleic acids, or used for detection of particular nucleic acid sequences and/or viruses in cells or tissues.

Batch or Continuous Conditions

The invention can be performed in commercially available equipment under batch or, less preferably, continuous flow stream, conditions; at elevated, reduced or atmospheric pressure and temperature, but atmospheric pressure and near ambient temperatures will be preferred for most applications.

Most large-scale bioseparations are done in batch because of the need to grow cells and the difficulty of maintaining a steady flow of cells from a chemostat, also the preparation will preferably be conducted under 50 degrees C. and more preferably under 25 C.

II. Utility of the Invention

The present invention is useful in the separation of DNA from RNA and vice versa. With numerous gene therapy products entering clinical trials, new and innovative strategies are needed to produce pure plasmid DNA.

In addition with the advances in gene chips in which DNA is attached to a small piece of glass (so that one chip can have over 1 million nucleic acid probes and can be used to test for disease) and genetic diagnostics, environmental monitoring, ribozyme research, and aptamers, improved separation processes for nucleic acid molecules are in demand.

The separation of RNA from bacterial cells is conventionally achieved by phenol/chloroform extraction and polyacrylamide gel electrophoresis. However, this conventional use of organic solvents and polyacrylamide (a neurotoxin) creates hazardous waste, and this approach is not easily scaleable for medium to large-scale production of RNA.

Selective precipitation by use of compaction agents according to the present invention provides lower cost, more effective and faster separation than the conventional methods of plasmid production. (See references 10 and 14) An added unexpected advantage of the selective precipitation of the invention is that it also contributes to improved performance of subsequent chromatographic columns used for further separation and purification.

Of considerable value in production of pharmaceuticals, the invention permits the precipitation of plasmid DNA containing less than 0.3 Units endotoxin per microgram plasmid DNA EU/$\mu$g or IE/$\mu$g).

BRIEF DESCRIPTION OF THE DRAWINGS

FIG. 2 shows schematically the precipitation by spermidine of 40 mg/mL PBGS19luxwt or Baker's yeast RNA in 10 mM Tris buffer at pH 8.0 with and without 600 mM NaCl. (Error bars are +/− one standard deviation.)

FIG. 3. Depicts a 1% agarose gel tracing the large-scale purification of pBGS19luxwt plasmid DNA. Lane 1 is a supercoiled plasmid ladder from Gibco; Lane 2 is the preparation after Celite filtration, isopropanol precipitation, and resuspension; Lane 3 is the supernatant after LiCl precipitation; Lane 4 is the supernatant of the compaction precipitation by 2.9 mM Spermidine HCl; Lane 5 is the resuspended pellet of the compaction precipitation after stripping of spermidine by 300 mM NaCl, 10 mM MgCl2, and 25 mM EDTA in 50% isopropanol; Lane 6 is a 10× loading of the material in Lane 5 (The traces of genomic DNA in these lanes can be removed by further optimization of the initial lysis and precipitation steps); Lane 7 is after a Q Sepharose anion exchange column (See FIG. 4, bottom, Peak 5); Lane 8 is a 10× loading of Lane 7 and Lane 9 is the same as Lane 1.

FIG. 4. Shows the chromatograms from a Pharmacia FPLC System using a HP Q Sepharose anion-exchange separation of pBGS19Luxwt of an alkaline lysate after isopropanol and LiCl precipitation and optional compaction precipitation. Top: NaCl gradient; Middle: with no previous compaction precipitation step; Bottom: identical separation after a compaction precipitation step (1 volume of 2.9 mM spermidine in 10 mM Tris HCl at pH 8.0; see example 1). A Spectrum chromatography column (2.5 cm×60 cm) packed with 150 mL Q Sepharose high performance and equilibrated in 10 column volumes of TE with 570 mM NaCl is used. Loading and elution are performed at a linear velocity of 90 cm/hr.

FIG. 5 shows schematically the process steps for separation of DNA as disclosed in Example 1.

FIG. 6. shows a 3% Biogel (from Bio101 Inc.) electrophoretic analysis of *V. proteolyticus* RNA purified by Example 9. Lane 1 is the Ambion RNA Century Plus Size Markers; Lane 2 is the lysate after BPER addition, spermidine addition and centrifugation; Lane 3 is the supernatant of the 4 mM hexammine cobalt precipitation; and Lane 4 is the RNA pelleted in the hexammine cobalt precipitation but before any column separation.

FIG. 7. shows a FPLC chromatogram of *V. proteolyticus* RNA on a 25 ml high performance Q Sepharose anion exchange column (Pharmacia). The gradient ran over 12 column volumes from 0.30 M NaCl to 0.57 M NaCl in a column buffer of 20 mM bis-tris propane and 20 mM EDTA at pH 6.9. (see Example 9)

FIG. 9 shows a FPLC chromatogram of selective precipitation purified β ribozyme on a 25 ml high performance Q Sepharose anion exchange column (Pharmacia). The gradient is run over 12 column volumes from 0.37 M NaCl to 0.7 M NaCl in a column buffer of 10 mM bis-tris propane and 2 mM EDTA at pH 6.9. (see Example 11)

Figure 1:
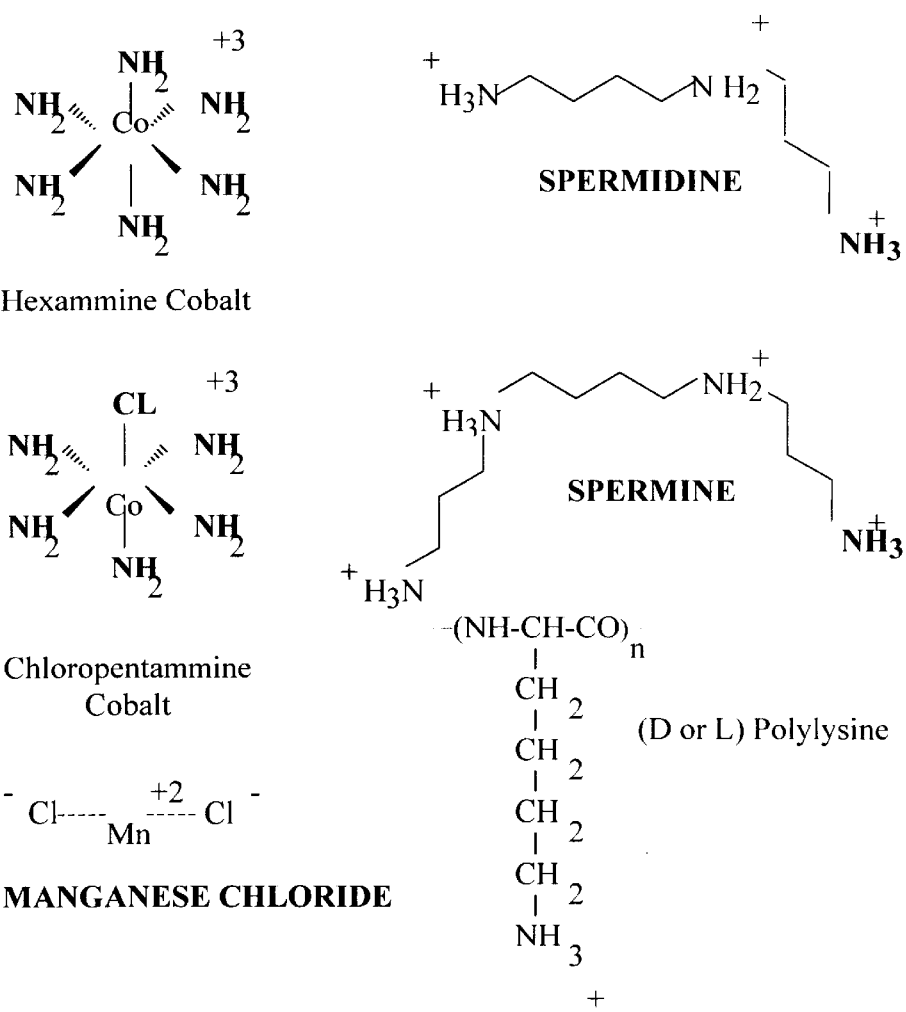
FIG. 1 is a schematic diagram of preferred structures of common compaction agents

Table A gives preferred, more preferred, and most preferred levels of some of the parameters of the invention.

DESCRIPTION OF THE PREFERRED EMBODIMENTS

EXAMPLE 1

Large-scale Plasmid Preparation

Referring to FIG. 5, *E. coli* JM109 strain containing pBGS19Luxwt plasmid grown in Pseudomonas Media 187 (per liter of media add 10 g tryptone, 10 g yeast extract, 5 g $K_2HPO_4$, 10 g glycerol, 5 ml salts solution to 1 L of distilled water where the salts solution contains 4.0 g $MgSO_4*7H_2O$, 0.2 g NaCl, 0.4 g $FeSO_4*7H_2O$, and 0.2 g $MnSO_4*4H_2O$ in 100 ml of H2O) at 37° C. in a 20 L Applikon fermentor (20 liter in-situ sterilizable bioreactor model number Z611120001). Overall fermentation time continues for about 12 hours and the cells grow to an $OD_{600}$ of about 20. The fermentor is harvested and the cells are pelleted at 4000 rpm in a Beckman centrifuge (6 L capacity rotor) for 30 minutes. Then the resulting pellets are optionally placed into plastic bags and heat-sealed to make crisps. The yield of the fermentation is approximately 440 g of wet cell paste.

Cells are lysed using a scaled-up version of the alkaline lysis procedure. First add 15 ml/gram wet cells of solution 1 (25 mM Tris Free Base, 10 mM EDTA, 50 mM Dextrose) and vortex. Next is added 15 ml/gram wet cells of Solution 2 (1% SDS and 0.2 N NaOH) and the mixture is inverted 2–3 times and put on ice for 5 minutes (being careful at this point because the nucleic acids are extremely shear sensitive at high pH). Finally, we add 15 ml/gram wet cells of solution 3 (which is 600 ml of 5 M KAc, 115 ml of glacial acetic acid, and 285 ml of distilled water per liter.) and invert 3–4 times and put on ice again for 5 minutes. The alkaline lysis not only disrupts the cells allowing DNA into solution but also most of the cellular proteins and chromosomal DNA are precipitated. At this point a white slime (mainly cell walls, precipitated protein, and precipitated chromosomal DNA) remains dispersed in the liquid.

At this point, a filtration is run to remove the cellular waste from the lysis step. 30 g/L Celite® Hyflo, a diatomaceous earth filter aid, are added to the product of the alkaline lysis and mixed with a plastic rod. The suspension is then filtered through Whatman #1 filter paper in a 12-cm plastic Buchner funnel. Next, the DNA is precipitated by adding 0.7 volume −20° C. isopropanol to the filtrate and centrifuging in 250 ml bottles at 15,000×g in a Beckmnan model J2-21 centrifuge for 10 minutes at 4° C. Pellets are allowed to dry by inversion for 10 minutes and each is resuspended in low ionic strength buffer (75 ml of 10 mM Tris buffer pH 8.0). An equal volume of 2.9 mM spermidine (spermidine trihydrochloride crystalline salt from Sigma Chemical, product number S 2501) solution in 10 mM Tris buffer pH 8.0 is added, the solution is mixed gently for 15 minutes at room temperature, and then centrifuged at 15,000×g for 10 minutes at 24° C. The supernatant is discarded, 25 ml of wash solution (50% isopropanol with 300 mM NaCl, 10 mM $MgCl_2$, and 25 mM EDTA) is added to the tube containing the pelleted DNA, and this solution is incubated for 15 minutes at room temperature before a final centrifugation at 15,000×g for 10 minutes at 4° C. The supernatant is discarded, the nucleic acids pelleted with 70% ethanol (to eliminate any residual salts) and then each pellet is resuspended in 10 ml of TE (10 mM Tris HCl, 1 mM EDTA, pH 8.0) with 570 mM NaCl.

The plasmid is loaded onto a Spectrum FPLC column (2.5 cm×60 cm) packed with 150 ml Q Sepharose high performance anion exchange matrix and equilibrated in 10 column volumes of TE with 570 mM NaCl using a Pharmacia Automated FPLC system (Pharmacia Code number 18-1040-00). Loading and elution are performed at a linear velocity of 90 cm/hr. The column is washed with 1 column volume of TE with 570 mM NaCl followed by 4 column volumes of TE with 600 mM NaCl. A linear gradient of NaCl (600 mM to 700 mM NaCl) in TE over 4 column volumes is used to elute the DNA. Absorbance is monitored at 254 nm and appropriate fractions are collected with a final yield of 6.5±0.1 mg/6 grams dry cell weight. In other experiments the yield is increased significantly by performing a temperature shift from 37 to 42° C. in the mid log phase of growth during the initial fermentation.

EXAMPLE 2

Plasmid Mini-prep

Three ml of LB (1 liter contains 10 g of tryptone, 5 g of yeast extract and 10 g of NaCl) medium containing 50 μg/ml kanamycin is inoculated with E. coli JM109 containing the plasmid pBGS19luxwt and grown overnight at 37° C. A 2 ml aliquot of this culture is pipetted into a 2 ml microcentrifuge tube and then centrifuged at 14,000×g for 5 minutes to pellet the cells. The cells are then resuspended and lysed by the alkaline lysis method. (see reference 10) 300 μl of solution 1 (25 mM Tris Free Base, 10 mM EDTA, 50 mM Dextrose) is added to the pellet and the pellet is resuspended by vortexing. After 300 μl of solution 2 (1% sodium dodecyl sulfate (SDS) and 0.2 N NaOH) are added and the mixture is inverted 3–4 times and placed on ice for 1–2 minutes.

Next 300 μl of ice-cold solution 3 (which is 600 ml of 5 M KAc, 115 ml of glacial acetic acid, and 285 ml of distilled water per liter.) is added and the mixture is inverted 3–4 times and again placed on ice for 1 minute. Then the solution is centrifuged in a tabletop Eppendorf centrifuge at maximum speed and the supernatant is poured off to a new tube. The resulting solution is precipitated with 0.7 volume of −20° C. isopropanol. The pellet is resuspended in 500 μl 10 mM Tris HCl at pH 8.0 and 500 μl of 2.9 mM spermidine (Spermidine trihydrochloride crystalline salt from Sigma Chemical product number S 2501) stock is added. The tube is vortexed 10 seconds, incubated for 1 minute and centrifuged at 14,000×g for 2 minutes. The supernatant is discarded and 400 μl of wash solution (50% isopropanol with 300 mM NaCl, 10 mM $MgCl_2$, and 25 mM EDTA) is added. The tube is again vortexed, incubated for 1 minute, and centrifuged at 14000×g for 3 minutes. The resulting pellet is washed with 70% ethanol and resuspended in 30 μl deionized $H_2O$.

EXAMPLE 3

Selective Precipitation

The concept of selective compaction precipitation is demonstrated by using salmon sperm DNA, pBGS19luxwt (a 6 B derivative of pUC19 expressing Vibrio harveyi luciferase), and total baker's yeast RNA. Both salmon sperm DNA (not shown) and the plasmid are efficiently precipitated with 0.5 mM spermidine at low ionic strength, but not in 600 mM NaCl. Yeast RNA, in contrast, does not precipitate at either ionic strength, as shown in FIG. 2. As practical applications will usually involve at least a modest ionic strength, the concentration of spermidine required to precipitate plasmid DNA in the presence of 100 mM NaCl is measured and found to be 5–10 mM spermidine.

EXAMPLE 4

Tetravalent Spermine

In other experiments conducted according to Example 3, plasmid DNA is precipitated in the presence of up to 200 mM NaCl substituting 10 mM of the (more potent) tetravalent spermine for spermidine.

EXAMPLE 5

Gram-scale Non-chromatographic Purification

Referring to FIG. 2, compaction precipitation used in a gram-scale non-chromatographic separation of plasmid DNA using the following steps: alkaline lysis (see reference 10), Celite filtration (see reference 11), isopropanol precipitation, LiCl precipitation (this step is optional), (see reference 12), isopropanol precipitation, compaction precipitation, and (if desired to remove compaction agents) washing with isopropanol/metal ion solution. In this procedure, the primary contribution of compaction precipitation is to remove the great majority of the RNA without the use of RNAse.

To eliminate compaction agent from the DNA pellet, several washing conditions have been examined. Preferably, a 50% isopropanol solution with 300 mM NaCl, 10 mM MgCl2 and 25 mM EDTA is used to remove spermidine. Removal of compaction agents can also employ non-alcoholic solutions of high ionic strength, and may be unnecessary for plasmids, which are to be formulated with spermine or spermidine for pharmaceutical delivery purposes. The selectivity of precipitation can be seen in FIG. 3, which illustrates the stages of a typical compaction agent based plasmid purification. Lane 4 of FIG. 3 shows the supernatant from compaction precipitation, while Lane 5 shows the resuspended pellet from the same precipitation and Lane 6, a 10-fold overload of the plasmid pellet in which only a small amount of RNA can be visualized. The compaction precipitation increases the percentage of DNA in the sample from approximately 2% to approximately 99%.

EXAMPLE 7

Effect of Compaction Precipitation on Subsequent Ion-exchange Polishing

Referring to FIGS. 3 and 4, anion-exchange chromatography is commonly used for final purification of plasmid DNA (see reference 13). It is found that RNA removal improves the throughput of subsequent ion-exchange columns for plasmid DNA reducing the resolution required to produce RNA-free plasmid. Anion-exchange chromatography is performed on a Pharmacia FPLC System to eliminate residual traces of RNA (FIG. 4). The selectively-precipitated plasmid, (10 mg plus the residual amount of RNA) resuspended in column running buffer and fractionated on a 150 mL Q Sepharose high performance anion-exchange column with the NaCl elution profile shown in FIG. 4 (top panel). The absorbance profile shown in the middle panel is the anion-exchange separation of resuspended isopropanol pellet not previously subjected to compaction precipitation, while the lower trace is the separation of material from which most RNA had been removed by a preliminary compaction precipitation step. The first two peaks are RNA passing through the column during the initial NaCl h and a step to 600 mM NaCl. The next peak (3) is a large RNA fragment, and the next two peaks are linear (4) and closed-circular plasmid (5) respectively, as determined by agarose gel electrophoresis (FIG. 3, lanes 7 and 8).

After compaction precipitation, the amount of RNA to be removed is greatly reduced, the loading capacity for plasmid DNA is higher (because of the lack of competing RNA) and the initial wash can be reduced in duration since very little RNA needs to be removed.

EXAMPLE 8

Small-scale Preparation of Plasmid DNA: "Mini-prep"

In addition to larger-scale pharmaceutical manufacturing, plasmid DNA is often purified on a smaller scale for sequencing and other purposes. With this in mind, another embodiment of the invention is a mini-prep protocol based on compaction precipitation, which is directly scaled down from large-scale protocol.

The detailed protocol is as follows:

1. Grow plasmid containing LB cell cultures overnight at 37° C. with proper agitation
2. Centrifuge 2 ml of at 14,200×g for 5 minutes and decant supernatant
3. Resuspend cell pellet in 300 µl of GTE solution (50 mM glucose, 25 mM Tris.HCl (pH 8.0), 10 mM EDTA (pH 8.0))
4. Add 300 µl of Alkaline Lysis solution (0.2 N NaOH and 1% SDS) and gently invert 3–4 times. Store on ice for 1–2 minutes.
5. Add 300 µl of neutralization solution (60 ml of 5 M KAc, 11.5 ml of glacial acetic acid, and 28.5 ml of distilled water per 100 ml of solution. Make sure to store at −20° C.) and allow it to sit for 1 minutes on ice.
6. Centrifuge at 14,200×g for 5 minutes and transfer supernatant to a new tube.
7. Add 0.7 volume of −20° C. isopropanol (0.84 ml), vortex and centrifuge at 14,200×g for 3 minutes
8. Decant supernatant and resuspend pellet in 400 µl of 10 mM Tris at pH 8.0.
9. Add 400 µl of 2.9 mM spermidine, vortex, incubate for 1 minute, and centrifuge at 14,200×g for 2 minutes.
10. Decant the supernatant
11. Wash the pellet with 800 µl of a fresh 50% IPA stock with 10 mM $MgCl_2$, 300 mM NaCl, and 25 mM EDTA. (I make up a stock of 20 mM $MgCl_2$, 600 mM NaCl, and 50 mM EDTA and add 1 volume of IPA before I do the preps. Beware that over the course of 2–3 hours the metal ions will precipitate from the washing solution so mix fresh solution as needed. Incubate for 1 minute and centrifuge for 2 minutes at 14,200×g.
12. Decant off wash solution.
13. Add 400 µl of 70% ethanol to wash the pellet. You may want to spin down the pellet for 20–30 seconds before decanting to make sure you do not lose the pellet.
14. Resuspend in buffer of choice.

The final product PCR-is sequenced successfully on an ABI model 377 sequencer, yielding approximately 600 bases of usable sequence information, and well digested by restriction enzymes EcoR I and Hind III.

EXAMPLE 9

Separation of Bacterial RNA

With the proper selective precipitation strategy and the proper gradient as we have developed means of fast purification for bacterial rRNA.

Cells are grown in LB medium (10 grams of tryptone, 5 grams of yeast extract and 10 grams of NaCl per liter of media) in 1 liter baffled shake flasks and the cultures are harvested in the mid-log phase ($OD_{600}$ 1.5 or less). Cells are then pelleted and stored at −80° C. until needed. Initial experiments are done on the wild type cell strain V. proteolyticus (see reference 29).

A non-ionic detergent mixture (BPER®) is used to lyse bacterial cultures. 60 mL of BPER® per liter of cells at $OD_{600}$=1 and is found effective in cell lysis. To these lysed cells 1 volume of 5 mM spermidine HCl buffered in 20 mM bis-tris propane (BTP) at pH 6.9 is added to the lysate to precipitate unwanted chromosomal and plasmid DNA. The initial lysis is helped by the addition of spermidine, which is also an anti-bacterial agent (see reference 34). This mixture is then centrifuged and the supernatant is poured off into a new tube for further purification.

To the clarified lysate 4 mM hexammine cobalt was added and vortexed for 1 minute then centrifuged and the supernatant was discarded. To remove hexammine cobalt from the RNA backbone, 50 mL of a 600 mM NaCl, 20 mM $MgCl_2$, and 50 mM EDTA buffered in 20 mM BTP at pH 6.9 was added. This solution is mixed for 2 minutes or until the pellet had redissolved. Next 2 volumes of ice cold EtOH are added to precipitate the RNA. Finally the RNA pellet is resuspended in 300 mM NaCl buffered in 10 mM BTP with 2 mM EDTA at pH 6.9 (column loading buffer). FIG. 6 is a 3% biogel (agarose) electrophoretic gel showing the separation after initial lysis and the supernatant and stripped pellet from the above detailed separation.

The RNA is loaded, using a Pharmacia FPLC System, onto an Amicon FPLC column (2 cm×8 cm) packed with 25 mL Q Sepharose high performance media and equilibrated in 10 column volumes of column buffer (20 mM bis-tris propane and 20 mM EDTA at pH 6.9). Loading and elution are performed at a linear velocity of 90 cm/hr. The column is washed with 4 column volumes of column loading buffer. RNA is eluted with a linear gradient of NaCl (300 mM to 570 mM NaCl in column buffer) performed over 10 column volumes. Absorbance is monitored at 254 nm and appropriate fractions are collected.

Nondenaturing anion-exchange chromatography can then be used to cleanup and separate each component of the rRNA fractions.

The anion-exchange columns use a high performance Q Sepharose strong anion exchanger from Pharmacia. FIG. 7 shows the absorbance profile obtained from a separation of V. proteolyticus RNA over the column. The column was loaded with selectively precipitated RNA enriched in rRNA. This allows the anion exchange column to resolve 5S rRNA from tRNA. This separation is very difficult unless the amount of tRNA is reduced before the anion exchange column is run. Peaks 3 and 4 are the 16S and 23S rRNA respectively. It is also possible to resolve the 16S and 23S rRNA on a nondenatured anion-exchange column as shown in FIG. 7 in the last two peaks.

EXAMPLE 10

Separation of Artificial Stable RNA

Artificial stable RNA (see references 20–22, 30) can be separated using the basic steps of Example 8 but with a few modifications. The aRNA pCP3X3 was produced in the E. coli JM109 and grown to an $OD_{600}$ from <1.5 in common LB media. Precipitation conditions and the procedure are identical to example 9 except for the anion-exchange column procedure. The anion-exchange column gradient is run between 0.30 M NaCl and 0.60 M NaCl all in a column buffer consisting of 20 mM bis-tris propane and 20 mM EDTA at pH 6.9 over 10 column volumes. The plot of 254 nm absorbance vs. volume from the FPLC system for this purification is shown in FIG. 7.

EXAMPLE 11

Separation of a Bacterially-expressed Ribozyme

Figure 8:
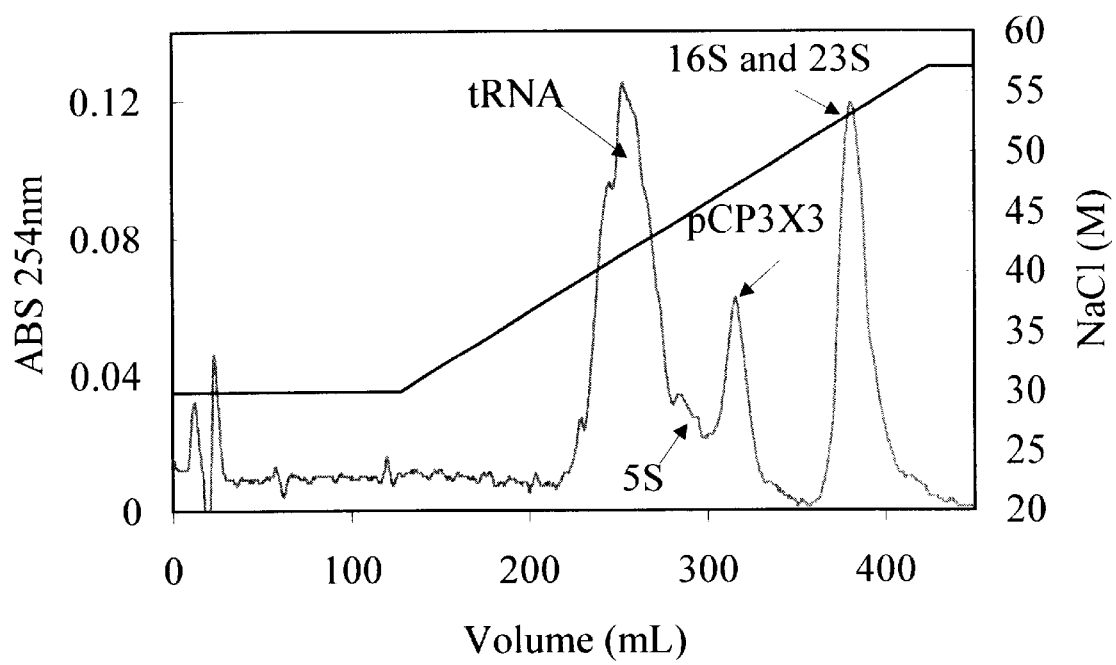
FIG. 8 shows a FPLC chromatogram of pCP3X3 aRNA-containing *E. coli* strain JM109 on a 25 ml high performance Q Sepharose anion exchange column (Pharmacia). The gradient is run over 12 column volumes from 0.37 M NaCl to 0.57 M NaCl in a column buffer of 20 mM bis-tris propane and 20 mM EDTA at pH 6.9. (see Example 10)

Ribozyme is produced using a T7-promoted plasmid. β ribozyme was produced in strain MPD92 containing the T7 promoter-based plasmid pMPD4. (reference 23) Expression of β ribozyme was induced by adding 1 mM ITPG of at OD>>0.4. All precipitation and lysis conditions are the same as example 9 but the anion exchange column. The column running buffer for this separation is 10 mM bis-tris propane with 2 mM EDTA at pH 6.9 (done to spread out the gradient.) The column is run from 0.3 M NaCl in column buffer to 0.65 M NaCl. The 254 nm absorbance vs. volume plot is shown in FIG. 8 and peak 1 corresponds to the β ribozyme. The problem with this separation is that the β ribozyme is 80 bases in length and cannot be resolved from tRNA and mRNA on an anion-exchange column as shown in FIG. 9. Alternative separation steps that can be tied are separation by size exclusion or hydroxyapatite chromatography (see references 31–33).

EXAMPLE 12

RNA Mini-prep

A RNA mini-prep is done with roughly the same concentrations of reagents detailed in Example 9 except on a much smaller scale, according to the following procedure. Many applications and variations to this mini-prep will be apparent to those skilled in the art. For instance, it can be done to produce total RNA and fractions of RNA enriched based on the size and amount of structure (double strandedness) of the RNA.

Protocol

1. Grow cells and harvest in mid log phase. (Maximizes RNA content)
2. Centrifuge at Max speed in a table top centrifuge for 5 minutes and decant supernatant (store at −80° C. if not used immediately)
3. Add 150 μl (15 ml/4 grams of wet cells) of BPER (Pierce, 78248) and resuspend pelleted cells by vortexing.
4. Incubate at room temperature for 2 minutes.
5. Add 150 μl of 2.9 mM spermidine HCl (Sigma, S-2501) buffered in 20 mM bis-tris Propane (BTP) at pH 6.9, vortex and incubate for 5 minutes.
6. Centrifuge at 12,000 rpm for 10 minutes at 4° C. (If necessary filter supernatant because the pellet has the consistency of jello.)
7. Decant supernatant to a new tube and add 300 μl of 4 mM Co(NH$_3$)$_6$ buffered in 20 mM BTP (Sigma, H-7891), vortex, and incubate for 5 minutes. (for total RNA use 7 mM Co(NH$_3$)$_6$ and for 16S and 23S rRNA use 2.5 mM Co(NH$_3$)$_6$)
8. Centrifuge at 12,000 rpm for 10 minutes at 4° C.
9. Decant supernatant and resuspend in 300 μl ml of stripping solution (600 mM NaCl, 10 mM MgCl$_2$, and 25 mM EDTA buffered in 20 mM BTP at pH 6.9 (all chemicals from Sigma)), vortex and incubate at room temperature for 3–5 minutes.
10. Add two volumes of ice-cold ethanol, vortex and, centrifuge at 10,000 rpm at room temperature for 5 minutes.
11. Decant supernatant and resuspend in buffer of choice.

EXAMPLE 13

Assay by Compaction Precipitated Probe Target Hybrids of 5S rRNA with Fluorescein Labeled Oligonucleotides The production of 5S RNA accomplished according to the protocol detailed in Example 12. The modification to the procedure of Example 12 occurs after the addition of 5 mM spermidine and before the addition of 4 mM hexammine cobalt. After step 6 in Example 12 and after the supernatant is added to a new tube ~10 nmols of 5' fluorescein labeled probe (5'-TGC-CTG-GCG-ACC-ATA-GCG-ATT-T-3') is added. This solution is then heated to 90 C. for 30 seconds and then rapidly cooled on ice. Then are carried out the rest of the steps in Example 13 but except resuspend in 300 μl of distilled H$_2$O in step 11. Next, using a microplate fluorometer with the proper filters for fluorescein the fluorescence is read in comparison with controls (e.g. same hybridization protocol with a strain of cell for which the probe will not bind and another without the labeled probe). If the correct target sequence is present the fluorescein emission will be well above background.

EXAMPLE 14

Clarification of Protein-containing Solutions

This example demonstrates (see reference 35) how DNA can be removed from lysates to aid in protein purification. First cells were grown in the Applikon fermenter (as in example 1) and the cells were an *E. coli* cell strain 1547 (a derivative of JM109). Approximately 120 grams of wet cells were resuspended in 20 mM HEPES buffer +0.1% Triton X-100 at pH 8.0 . Then the lysate is run through a French cell press twice to lyse cells. After lysis, 6 mL of 0.5 M spermidine HCl solution is added and the overall pH was readjusted to 8.0. Next the lysate is spun down at 12,000×g in a Beckman J2-21 centrifuge at 4 C. This cleared lysate is run over a 300 ml High performance Q sepharose column at a flow rate of 10 mL/minute and an optimized gradient for proteins eluted. After spermine precipitation the lysates are visibly less viscous, have a negligible amount of nucleic acid remaining as checked using agarose gel electrophoreses and protein concentrations are identical to that of the untreated solution as determined by BioRad's Protein Assay (a Bradford Assay).

EXAMPLE 15

Mini-prep from Difficult Host Strains

The techniques of Examples 1 and 2 are applied to host strains that are difficult to separate nucleic acids from, in this example, the strain of Pseudomonas LD2 which has a polysaccharide coat on its outer membrane. This cell strain is extremely hard to process using conventional technology since the polysaccharides will co-purify with the plasmid DNA, chromosomal DNA, etc. The selective precipitation done according to Examples 1 and 2 is an extremely effective separation on both the large and small scale for these hard to purity host strains. The protocols in Examples 9 and 12 can also be applied to purify RNA from these same hard to purify strains.

EXAMPLE 16

Isolation of Nucleic Acid-binding Proteins

This example demonstrates the use of compaction precipitation to produce an enriched sample of a nucleic-acid-binding protein, (this protein is a DNA-binding repressor which binds to a lac repressor found in the plasmid). *E. coli* cells harboring plasmid encoding a protein with affinity for a DNA sequence found in the plasmid were grown m the Applikon fermenter (as in example 1). Approximately 120 grams of wet cells were resuspended in 20 mM HEPES buffer +0.1% Triton X-100 at pH 8.0 , and the lysate is run through a French cell press twice to lyse cells. Next the lysate is spun down at 12,000×g in a Beckman J2-21 centrifuge at 4 C. After centrifugation, 6 mL of 0.5 M spermidine HCl solution is added to the supernatant and the overall pH is readjusted to 8.0. Next the precipitate is spun down at 12,000×g in a Beckman J2-21 centrifuge at 4 C. Resuspension of the pellet resulting from this centrifugation results in a solution enriched in the DNA-binding protein.

EXAMPLE 17

Separation of Natural Plasmids for Quick Recognition of Degradative Pathways

The process of Examples 1 and 2 is applied to the separation of natural plasmids from pseudomonas cells, which, encode for an aromatic degradative pathway. The isolated plasmids are used in efficiently searching for the genes encoding the degradative pathway.

EXAMPLE 18

Large-scale (Low Endotoxin) Plasmid Preparation

In other experiments conducted according to Example 1, the resuspended plasmid product is found by the Pyrochrome(R) (Chromagenic Formulation) Limulus Amebocyte Lysate (LAL) assay (Associates of Cape Cod, Inc.) to contain less than 0.3 Units endotoxin per microgram plasmid (EU/$\mu$g or IE/$\mu$ug).

EXAMPLE 20

Additional Washing

Additional washing steps are can be added to Example 1 such that the end sample contains less than 0.1 Units endotoxin per microgram plasmid. 70% EtOH or a 1.5 mM spermidine rinse after initial pelleting by compaction precipitation is used as a washing step for plasmid during the process.

EXAMPLE 21

Multiple Compaction Precipitations

Example 1 is can be augmented by performing the main process of compaction agent precipitation multiple times in series to provide plasmid containing less than 0.1 Units endotoxin per microgram plasmid. Also reduced levels of other contaminants (e.g. RNAse, RNA, proteins, DNAse) are obtained possible with multiple compaction precipitations.

EXAMPLE 22

Tetravalent Spermine (Low Endotoxin)

In other experiments conducted according to the process of Example 3, plasmid DNA is precipitated in the presence of up to 200 mM NaCl by substituting 10 mM of the (more potent) tetravalent spermine for spermidine. The resuspended plasmid product is found by the Pyrochrome(R) (Chromagenic Formulation) Limulus Amebocyte Lysate (LAL) assay (Associates of Cape Cod, Inc.) to contain less than 0.3 Units endotoxin per microgram plasmid DNA (EU/$\mu$g or IE/$\mu$g). Refined procedures or repeated precipitations provide product containing less than 0.1 Units endotoxin per microgram plasmid DNA (EU/ug or IE/ug).

MODIFICATIONS

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein. For example, another potential application of selective precipitation is to the isolation of RNA; preliminary work indicates that potent compaction agents can not only precipitate RNA but also fractionate different sized RNA molecules. Finally, compaction agent may substitute for protamine, streptomycin, etc. in cleaning up cell lysates for purification of intracellular proteins. In the above Examples we have demonstrated that addition of a compaction agent can precipitate DNA or RNA from crude cell lysates, greatly reducing product viscosity and improving the performance of subsequent chromatographic columns, see e.g. Example 14.

Most preferably, the invention comprises a method of preparing substantially purified DNA, without the use of nucleases or proteases, (more preferably free of animal-derived proteins or free of non-host-derived ribonucleases), by adding an effective amount of a compaction agent to a lysate so as to precipitate from said lysate, DNA having a content of RNA of less than 3% by weight.

Using compaction precipitation, when a tagged probe (e.g. fluoresceinated probe) is added to a solution containing its target, a double stranded nucleic acid is formed and this new structured hybrid can be selectively precipitated while the single stranded probe will be left in solution.

A particularly preferred application of the protocols of the invention is for producing pharmaceutical grade plasmid DNA with an RNAse level, chromosomal DNA level, contaminating protein level, an endotoxin level and a RNA level below the guidelines set forward by the U.S. Food and Drug Administration, (see e.g. the FDA website at http://www.fda.org/).

Reference to documents made in the specification is intended to result in such patents or literature being expressly incorporated herein by reference.

TABLE A

| Parameter | Units | Preferred | Most Pref. |
|---|---|---|---|
| Cell Mass | | Archaea eukaryotes bacterial, Gram-negative Gram-positive phage, yeast | Gram-neg |
| Product: | | DNA, RNA, Assay NA-binding protein enzymes, cosmids, YACs, Plasmid | plasmid DNA |
| Compaction Agent: basic polypeptides (e.g. polylysine), polyamines (e.g. protamine, spermidine, spermine, putrescine, cadaverine, etc.), trivalent and tetravalent metal ions (e.g. hexammine cobalt, chloropentammine cobalt, chromium (III)), netropsin, distamycin, lexitropans, DAPI (4',6 diamino 2-phenylindol), berenil, pentamidine, manganese chloride. Most preferred: hexammine cobalt, spermine and spermidine | | | |
| CA Conc. mM | | 0.02–20 | 0.05–10 |
| ysing Agent: detergent | | nonionic det. | BPER for RNA; (alkaline lysis is m.p. for plasmid DNA) |
| ysing Agent: Conc.: wt % | | 0.5–2 | .05–.5 |
| pH: varies | | 6–8 | 7 |
| Ionic Strength: mM (Before Compaction) | | 0–200 | 0–50 |
| Endotoxin Level | | >0.3 EU/ml | >0.1 EU/ml |

What is claimed is:

1. A method of preparing substantially purified DNA, without the use of nucleases or proteases, or organic solvent extraction, comprising adding an effective amount of a compaction agent selected from the group consisting of: basic polypeptides, polyamines, trivalent and tetravalent metal ions to a lysate containing DNA to selectively precipitate from said lysate, plasmid-DNA, chromosomal-DNA, or oligonucleocidal-DNA having a content of RNA of less than 3% by weight.

2. A method for the production without the use of nucleases or proteases or organic solvent extraction, of purified DNA having a content of RNA of less than about 3% by weight, comprising in combination the following steps:
   A. lysing a cell mass to liberate the nucleic acids;
   B. optionally precipitating some additional moieties;
   C. optionally adjusting the ionic strength and/or plasmid concentration; and;
   D. adding an effective amount of a compaction agent to precipitate a substantial fraction of the DNA away from contaminating RNA and protein.

3. A method of treatment of a mixture comprising desired RNA product and contaminating DNA comprising mechanical lysis of the mixture in the presence of a compaction agent to precipitate at least a portion of the contaminating DNA.

4. A method according to claim 2 wherein DNA is separated from endotoxin to a level of less than 0.1 EU/μg plasmid DNA.

5. A method according to claim 3 for producing ribosomal RNA, chromosomal DNA, plasmid DNA, aptamer, artificial RNA, or mRNA.

6. The method of claim 1 comprising producing plasmid having an undetectable content of ribonucleases by standard assays.

7. The method of claim 1 comprising producing plasmid having a content of eukaryotic ribonucleases of less than 0.001% weight.

8. The method of claim 1 in which the addition of the compaction agent comprises the addition of two or more different mixed compaction agents whereby improved separation efficiency results.

9. The method of claim 1 further comprising subsequent chromatographic column purification wherein prior use of compaction agents enhances the overall loading capacities of plasmid DNA on anion-exchange columns by elimination of the majority of contaminating RNA and other biomolecules, which would otherwise impair the subsequent chromatography.

10. A method according to claim 1 additionally comprising stripping the compaction agent by a stripping method selected from the group comprising high salt addition and/or a pH shift.

11. A method according to claim 2 wherein the method is applied to remove large nucleic acid molecules from low ionic strength bacterial lysates.

12. A method according to claim 2 additionally comprising a technique selected from the group consisting of: use of French cell press, addition of nonionic detergent, lysozyme addition, microfluidizer, freeze-thaw or any other relatively low ionic strength lysis technique to produce nucleic acid free lysates for later protein recovery.

13. A method according to claim 1 comprising simultaneous application of the method in parallel mini-prep procedures for a plurality of cell masses.

14. A method according to claim 2 producing plasmid DNA with an RNAse level, chromosomal DNA level, contaminating protein level, an endotoxin level and a RNA level below the guidelines set forward by the Food and Drug Agency.

15. A method according to claim 2 additionally comprising a further separation step comprising one or more techniques selected from the group consisting of: precipitation and resuspension, filtration and adsorption for production of more pure product.

16. A method according to claim 2 comprising addition of about 0.001 to 20 mM of a compaction agent selected from the group consisting of: basic polypeptides (e.g. polylysine), polyamines (e.g. protamine, spermidine, spermine, cadaverine), trivalent and tetravalent metal ions (e.g. hexammine cobalt, chloropentammine cobalt, chromium (III)), netropsin, distamycin, lexitropans, DAPI (4', 6 diamino 2-phenylindol), berenil, pentamidine, or manganese chloride).

17. The method of claim 2 wherein the cell mass comprises nucleic acid or a synthesized analog.

18. The method of claim 2 wherein the source of the lysate is selected from the group consisting of gram negative bacteria, gram-positive bacteria, yeast, eukaryote, synthesized nucleic acids, Archaea, bacteria, protozoa, phages, other viruses, human cells, body fluids, mixtures of cells, tissues, and environmental samples.

19. A method according to claim 16 comprising precipitating a substantial fraction of the DNA away from contaminating RNA and protein by addition of the compaction equivalent of one volume of from 1 to 10 mM spermidine in the form of a compaction agent.

20. The method of claim 3 comprising producing plasmid having an undetectable content of ribonucleases by standard assays.

21. The method of claim 3 comprising producing plasmid having a content of eukaryotic ribonucleases of less than 0.001% by weight.

22. The method of claim 3 in which the addition of the compaction agent comprises the addition of two or more different mixed compaction agents whereby improved separation efficiency results.

23. The method of claim 3 further comprising subsequent chromatographic column purification wherein prior use of compaction agents enhances the overall loading capacities of plasmid DNA on anion-exchange columns by elimination of the majority of contaminating RNA and other biomolecules, which would otherwise impair the subsequent chromatography.

24. A method according to claim 3 additionally comprising stripping the compaction agent by a stripping method selected from the group comprising high salt addition and/or a pH shift.

25. A method according to claim 3 wherein the method is applied to remove large nucleic acid molecules from low ionic strength bacterial lysates.

26. A method according to claim 3 comprising a technique selected from the group consisting of: use of French cell press, addition of nonionic detergent, lysozyme addition, microfluidizer, freeze-thaw or any other relatively low ionic strength lysis technique to produce nucleic acid free lysates for later protein recovery.

27. A method according to claim 3 comprising simultaneous application of the method in parallel mini-prep procedures for a plurality of cell masses.

28. A method according to claim 3 producing plasmid DNA with an RNAse level, chromosomal DNA level, contaminating protein level, an endotoxin level and a RNA level below the guidelines set forward by the Food and Drug Agency.

29. A method according to claim 3 additionally comprising a further separation step comprising one or more techniques selected from the group consisting of: precipitation and resuspension, filtration and adsorption for production of more pure product.

30. A method according to claim 3 comprising addition of about 0.001 to 20 mM of a compaction agent selected from the group consisting of: basic polypeptides (i.e. polylysine), polyamines (i.e. protamine, spermidine, spermine, cadaverine, etc.), trivalent and tetravalent metal ions (i.e. hexammine cobalt, chloropentammine cobalt, chromium (III)), netropsin, distamycin, lexitropans, DAPI (4', 6 diamino 2-phenylindol), berenil, pentamidine, or manganese chloride.

31. The method of claim 3 wherein the cell mass comprises nucleic acid or a synthesized analog.

32. The method of claim 3 wherein the source of the lysate is selected from the group consisting of gram-positive bacteria, yeast, eukaryote, synthesized nucleic acids, Archaea, bacteria, protozoa, phages, other viruses, human cells, body fluids, mixtures of cells, tissues, or environmental samples.

33. A method according to claim 3 comprising addition of the compaction equivalent of one volume of from 1 to 10 mM spermidine in the form of a compaction agent.

* * * * *